United States Patent [19]

Lin et al.

[11] Patent Number: 4,791,135

[45] Date of Patent: Dec. 13, 1988

[54] NOVEL ANTIMALARIAL DIHYDROARTEMISININ DERIVATIVES

[75] Inventors: Ai J. Lin, Gaithersburg; Daniel L. Klayman, Chevy Chase; Wilbur K. Milhous, Rockville, all of Md.

[73] Assignee: The United States of America as represented by the Secretary of the Army, Washington, D.C.

[21] Appl. No.: 87,365

[22] Filed: Aug. 20, 1987

[51] Int. Cl.[4] ................ C07D 493/18; A61K 31/335
[52] U.S. Cl. ..................................... 514/450; 549/348
[58] Field of Search ...................... 549/348; 514/450

[56] References Cited
PUBLICATIONS

Klayman, Science, vol. 228, pp. 1049–1955, 1985.
Zhou. Wei-Shan, Pure and Applied Chemistry, vol. 58, No. 5, pp. 817–824, 1986.
Song, CA 103: 205354k.
Yu, CA 98: 4420h.

Primary Examiner—Jane T. Fan
Attorney, Agent, or Firm—Anthony T. Lane; William V. Adams; Werten F. W. Bellamy

[57] ABSTRACT

This invention relates to novel dihydroartemisinin derivatives, including their pharmaceutically-acceptable salts, which are therapeutically-effective in the pre- and post-treatment of malarial infections.

8 Claims, No Drawings

NOVEL ANTIMALARIAL DIHYDROARTEMISININ DERIVATIVES

GOVERNMENT INTEREST

The invention described herein may be manufactured, licensed and used by or for the government for governmental purposes, without the payment of any royalties to us thereon.

BACKGROUND OF THE INVENTION

The usefulness of the water-soluble composition, artesunic acid (compound 1) in the form of its sodium salt, is impaired by its poor stability in aqueous solution.

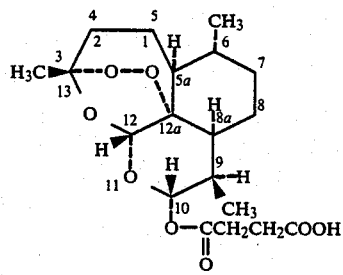

Artesunic Acid (Compound 1)

compound 1 is derived from dihydroartemisinin (compound 2) having the formula

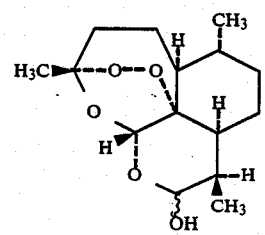

Dihydroartemisinin (Compound 2)

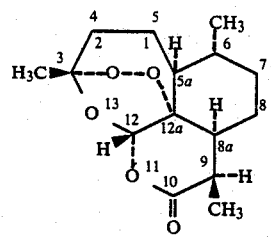

Artemisinin (Compound 3)

which, in turn, is prepared from artemisinin (compound 3). To overcome the ease of hydrolysis of the ester group in artesunic acid, the applicants have prepared novel derivatives of dihydroartemisinin. In these derivatives, the solubilizing moiety contains a carboxylate group, and is joined to dihydroartemisinin by an ether, rather than an ester, linkage.

SUMMARY OF THE INVENTION

The novel compounds were prepared in accordance with this invention by treating dihydroartemisinin with an appropriate alcohol, which also contains an ester functional group, under boron trifluoride etherate catalysis at room temperature. Hydrolysis of the ester group with 2.5% KOH/MeOH gave the corresponding potassium salts which were converted to free acids, designated herein as compounds (8b–d), by acidification.

The derivatives were tested in vitro against 2 clones of human malaria, *Plasmodium falciparum* D-6 (Sierra Leone clone) and W-2 (Indochina clone). No cross-resistance to the antimalarial agents mefloquine, chloroquine, pyrimethane, sulfadoxine and quinine was observed. In general, the new compounds are more effective against the multi-drug resistent W-2 clone, than the D-6 clone. The esters, designated herein as compounds 5a–d, possess activity comparable to that of the parent compound 3; however, conversion of the esters to their corresponding carboxylates designated herein as compounds 7a–d, or acids compounds 8b–d, with the exception of artelinic acid compound 8d, drastically decreases the antimalarial activities in both cell lines. Salts of artelinic acid, such as its alkali metal salt, are water soluble, stable in 2.5% $K_2CO_3$ solution, and possess in vitro activity comparable to that of artemisinin.

Artemisinin (ginghaosu), a clinically useful antimalarial agent which was isolated from the plant *Artemisia annua*, is an unusual sesquiterpene lactone containing an epidioxide function. Dihydroartemisinin (2), obtained by sodium borohydride reduction of artemisinin (3), has been reported to be more therapeutically active than its parent compound. Neither artemisinin nor dihydroartemisinin exhibit cross-resistance to chloroquine and both were proven efficacious against cerebral malaria in man. Sodium artesunate, the sodium salt of the succinic acid half ester derivative of dihydroartemisinin, is water soluble and can be administered by intravenous injection, making the compound particularly useful in the treatment of cerebral malaria where rapidity of administration is critical. The utility of sodium artesunate is, however, impaired by its poor stability in aqueous solution due to the ready hydrolysis of the ester linkage.

To overcome the stability problem, applicants carried out the extensive research necessary to make a series of new water-soluble and stable derivatives, in which the carboxylate solubilizing group is on a moiety which is joined to dihydroartemisinin by an ether, rather than an ester linkage.

DETAILED DESCRIPTION OF THE INVENTION

This invention relates to the preparation and use of the following compounds and their pharmaceutically-acceptable salts in the pre- and/or post-treatment of malarial infections:

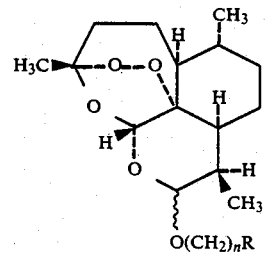

or a pharmaceutically-acceptable salt, including alkali and alkaline earth metal salts and the like, thereof wherein R is

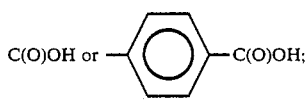

and n represents the positive integers 1 to 7, preferably 1,2 or 3. In this disclosure, it is understood that C(O)OH represents the carboxylic acid moiety.

A partial recitation of specific antimalarial compounds contemplated within the scope of applicant's invention are depicted by the following formula:

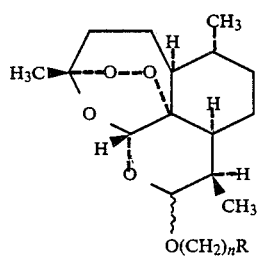

wherein R represents

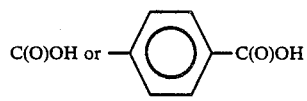

and n represents the positive integers 1 to 7, preferably 1,2 or 3 and their pharmaceutically-acceptable salts.

The chemical nomenclature for certain of the antimalarials included within the formula depicted in preceeding paragraph include:

2-(10-Dihydroartemisininoxy)acetic acid (compound 8a);

3-(10-Dihydroartemisininoxy)propionic acid (compound 8b);

4-(10-Dihydroartemisininoxy)butyric acid (compound 8c);

para-(10-Dihydroartemisininoxy)methylbenzoic acid (compound 8d);

and the corresponding pharmaceutically-acceptable salts thereof.

The compound designated herein above as compound 8d is also referred to as artelinic acid.

The compounds described above and their pharmaceutically-acceptable salts are useful in the treatment of malarial infections.

With respect to the pharmaceutically-acceptable salts of this invention, it will be apparent to those of ordinary skill in the art that such salts are contemplated only where the structural features of the compounds permit their preparation. As nonlimiting examples of bases used to prepare such salts are sodium carbonate or potassium hydroxide.

SYNTHETIC PROCEDURE

The synthetic procedure proved to be useful for preparing the water-soluble dihydroartemisinin derivatives of this invention is discussed and illustrated in the chemical reaction scheme below.

Discussion

Dihydroartemisinin (compound 2) was prepared by sodium borohydride reduction of compound 3 according to a modified literature procedure disclosed by J. Liu et al. in *Acta Chimica Sinica,* 1979, Volume 37 at page 129. The peroxide group is not affected by the sodium borohydride treatment. Inasmuch as dihydroartemisinin is a hemiacetal (lactol), it exists as a mixture of alpha- and beta-isomers whose ratio is solvent-dependent.

The new ether derivatives of dihydroartemisinin (compounds 5a-d) were prepared by treatment of (compound 2) with an appropriate alcohol-ester (compound 4) under the catalysis of boron trifluoride etherate at or near room temperature. The yield of the purified condensation products (compounds 5a-d) ranged from 70-90%. A minor product (compound 6a or 6b), depending on whether the alcohol-ester (compound 4) is a methyl or ethyl ester, was also isolated in some of the reactions. The source of methanol or ethanol for the formation of compounds 6a or 6b is very likely generated from partial transesterification or lactone formation of the alcohol-ester (compound 4) used. All major condensation products (compound 5) are the beta-isomer as indicated by the small coupling constants between 10-H (J=3-4 Hz) and 9-H as described by Y. Li et al., *Acta Pharm. Sinica,* 1981, Volume 16 at page 429. Due to the close proximity to several asymmetric carbon centers on the dihydroartemisinin moiety, the two methylene protons on carbon alpha to the new ether oxygen are non-equivalent and thus appears as an AB quartet. A large geminal coupling constant (J=12.6 Hz) and chemical shift difference ($\Delta\delta=0.4$ ppm) between the two benzylic protons of compound 5d was observed. Likewise, a large coupling constant between the methylene protons alpha to the ether oxygen of compounds 5b and 5c can be measured by a decoupling technique. A similar observation has been disclosed in the literature. However, the corresponding methylene protons of compound 5a appears as a singlet, a surprising exception.

Hydrolysis of the ester (compound 5a) with 2.5% KOH/MeOH gave the corresponding potassium salt which was purified by reverse phase chromatography. Conversion of the salt (compound 7a) to the free acid (compound 8a) was achieved by acidification with acetic acid. The free acid appears to be unstable, as evidenced by gradual changes seen in its PMR spectrum on standing. This may be due to the instability of the acetal or ketal functions of the molecule under acidic conditions. In contrast, compounds 7b through 7d were smoothly converted to their corresponding stable free acids (compounds 8b-d).

To compare the relative stability of the new agents vs. artesunic acid, stability studies of compound 8d and compound 1 were conducted in 2.5% $K_2CO_3/D_2O$ solution at room temperature and were monitored by PMR.

Chemical Reaction Scheme

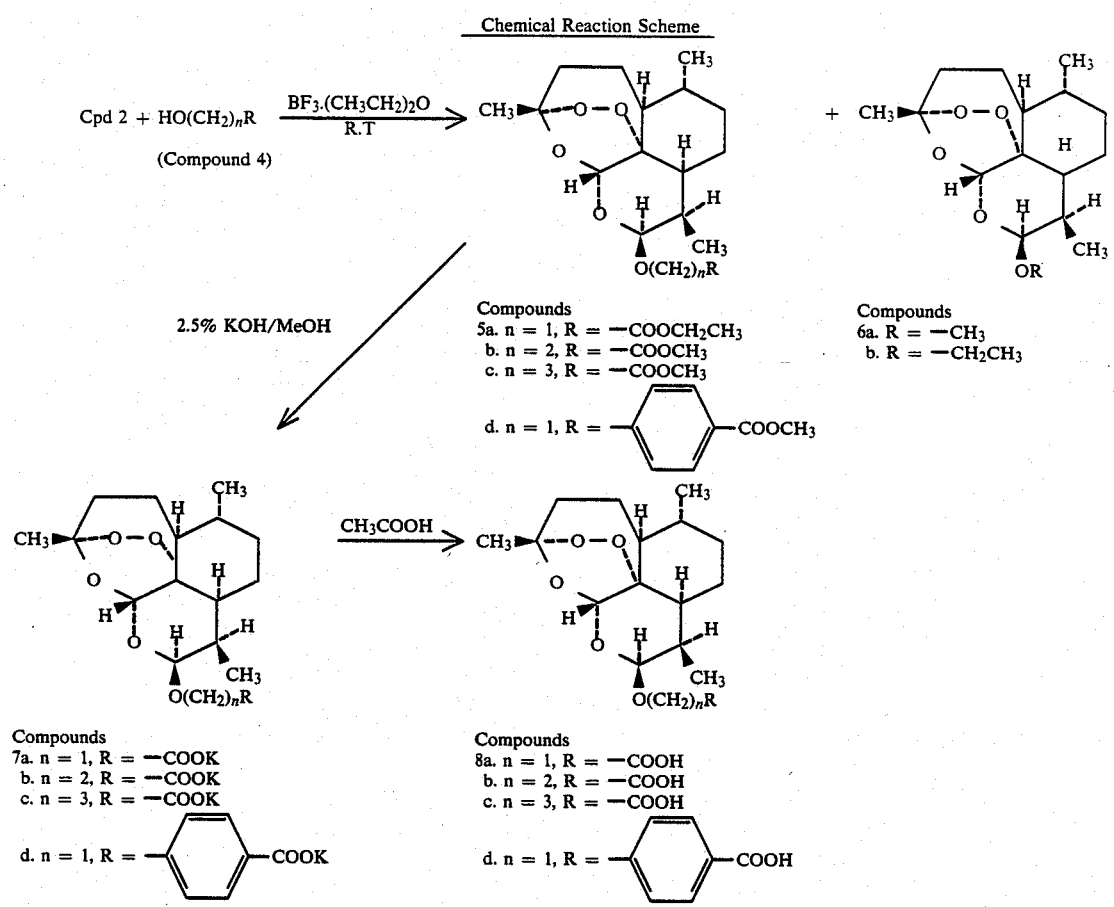

Compounds
5a. n = 1, R = —COOCH$_2$CH$_3$
b. n = 2, R = —COOCH$_3$
c. n = 3, R = —COOCH$_3$ d. n = 1, R = —[C$_6$H$_4$]—COOCH$_3$ Compounds
6a. R = —CH$_3$
b. R = —CH$_2$CH$_3$ Compounds
7a. n = 1, R = —COOK
b. n = 2, R = —COOK
c. n = 3, R = —COOK d. n = 1, R = —[C$_6$H$_4$]—COOK Compounds
8a. n = 1, R = —COOH
b. n = 2, R = —COOH
c. n = 3, R = —COOH d. n = 1, R = —[C$_6$H$_4$]—COOH

WORKING EXAMPLES

The working examples set forth below illustrate the preparation of representative compounds and salts, but in no way limit the scope of the invention.

All melting points were determined on a Thomas-Hoover melting point apparatus and are uncorrected. Infrared spectra of solid samples were obtained in KRr disks on a Perkin-Elmer Model 283 spectrophotometer. NMR spectra were run on a JEOL-FT90Q spectrometer.

EXAMPLE 1

Dihydroartemisinin (Compound 2)

Artemisinin (compound 3) (0.5 g, 1.8 mmole) in 40 mL of MeOH was cooled in an ice-bath to 0°–5° C. To the solution was added in small portions 0.25 g (6.6 mmole) of NaBH$_4$ over a period of 30 minutes. The solution was stirred at 0°–5° C. for 2 hours after the addition of NaBH$_4$ was complete. The solution was neutralized with 30% AcOH/MeOH and evaporated to dryness under reduced pressure. The white residue was extracted 3 times with 50 mL of EtOAc. The EtOAc extracts were combined, filtered, and evaporated to dryness to give 0.38 g (75%) of white needles mp 152°–154° C. (dec). Recrystallization from EtOAc-hexane raised the melting point to 153°–155° C. (lit. mp 153°–154° C.).

EXAMPLE 2

Ethyl 2-(10-Dihydroartemisininoxy)acetate (Compound 5a)

Dihydroartemisinin (compound 2) (0.5 g, 1.75 mmole) was dissolved in 70 mL of anhydrous Et$_2$O. To the solution was added successively 0.5 g (5 mmole) of ethyl glycolate and 0.25 mL of BF$_3$.Et$_2$O. The reaction mixture was stirred at room temperature for 24 hours, washed successively with 5% aqueous NaHCO$_3$ and H$_2$O, dried over Na$_2$SO$_4$, and evaporated to dryness under reduced pressure. The resultant oil was purified by preparative TLC using EtOAc-hexane (1:3 volume/volume (v/v) to give 0.45 g (68%) of compound 5a, mp 50°–52° C.; IR (neat) 1755 cm$^{-1}$ [—OC(=O)]; $^1$H NMR (CDCl$_3$) δ5.53 (s, 1H), 4.87 (d, J=3.6 Hz, 1H), 4.26 (s, 2H), 4.18 (q, J=7.2 Hz, 2H), 2.68 (m, 1H), 1.43 (s, 3H), 1.27 (t, J=7.2 Hz, 3H), 1.01 (d, J=4.5 Hz, 3H), and 0.93 (d, J=1.8 Hz, 3H). Anal. Calcd. for C$_{19}$H$_{30}$O$_7$: C, 61.62; H, 8.11. Found: C, 62.09; H, 8.09.

The minor product (22% yield), with a higher Rf value than compound 5a, was identified by NMR as arteether (compound 6b); $^1$H NMR (CDCl$_3$) δ0.90 (d, J=7.2 Hz, 3H), 0.96 (d, J=3.6 Hz, 3H), 1.18 (t, J=7.2 Hz, 3H), 1.43 (s, 3H), 2.61 (m, 1H), 3.47 (m, 1H), 3.85 (m, 1H), 4.84 (d, J=3.6 Hz, 1H) and 5.40 (s, 1H); $^{13}$C NMR (CDCl$_3$) ppm 12.86, 15.08, 20.23, 24.34, 24.61, 26.08, 30.74, 34.58, 36.37, 37.35, 44.44, 52.51, 63.62, 81.01, 87.73, 101.54, and 103.88.

EXAMPLE 3

Methyl 3-(10-Dihydroartemisininoxy)propionate (Compound 5b)

The procedure for the preparation of compound 5a was used to prepare compound 5b by treating 0.5 g (1.75 mmole) of compound 2 with 1 (9.6 mmole) of methyl 3-hydroxypropionate. It yielded 460 mg (70%) of the desired product as an oil after purification by preparation TLC (silica gel, EtOAc-hexanes 1:2 v/v). The compound solidified on standing, mp 76°-78° C.; IR (neat) 1743 cm$^{-1}$ [—OC(=O)]; $^1$H NMR (CDCl$_3$) δ5.43 (s, 1H), 4.80 (d, J=3.3 Hz, 1H), 4.10 (m, 1H), 3.68 (s, 3H), 3.67 (m, 1H), 2.58 (t, 2H), 1.44 (s, 3H), 0.95 (d, J=6.3 Hz, 3H), and 0.87 (d, J=7.2 Hz, 3H), Anal. Calcd. for C$_{19}$H$_{30}$O$_7$: C, 61.62; H, 8.11. Found: C, 62.03; H, 8.07.

EXAMPLE 4

Methyl 4-(10-Dihydroartemisininoxy)butyrate (Compound 5c)

The same procedure for the preparation of compound 5a was used to prepare compound 5c. Treatment of 1 g (8.5 mmole) of methyl 4-hydroxybutyrate with 0.5 g (1.75 mmole) of compound 2 gave 70% of the desired product as an oil after purification. IR (neat) 1740 cm$^{-1}$ [—OC(=O)]; $^1$H NMR (CDCl$_3$) δ5.38 (s, 1H), 4.77 (d, J=3.6 Hz, 1H), 3.85 (m, 1H), 3.68 (s, 3H), 3.34 (m, 1H), 1.43 (s, 3H), 0.96 (d, J=3.6 Hz, 3H) and 0.90 (d, J=7.2 Hz, 3H). Anal. Calcd. for C$_{20}$H$_{32}$O$_7$: C, 62.50; H, 8.33. Found: C, 63.13; H, 8.64.

The minor product, with a higher Rf value than compound 5c, in 22% yield was identified by NMR as artemether (compound 6a); $^1$H NMR (CDCl$_3$) δ0.90 (d, J=6.3 Hz, 3H), 0.96 (d, J=2.7 Hz, 3H), 1.44 (s, 3H), 2.6 (m, 1H), 3.42 (s, 3H), 4.68 (d, J=3.6 Hz, 1H) and 5.38 (s, 1H); $^{13}$C NMR (CDCl$_3$): ppm 12.95, 20.37, 24.49, 24.70, 26.22, 30.93, 34.67, 36.46, 37.43, 44.53, 52.60, 55.60, 81.10, 87.76, 103.36, and 104.07.

EXAMPLE 5

Methyl p-(10-Dihydroartemisininoxy)methylbenzoate (Compound 5d)

Treatment of 1 g (6.0 mmole) of methyl p-hydroxymethylbenzoate and 0.5 g (1.75 mmole) of compound 2 as given for the preparation of compound 5a gave compound 5d in 89% yield as an oi; IR (neat) 1725 cm$^{-1}$ [—OC(=O)]; $^1$H NMR (CDCl$_3$) δ8.02 (d, J=9.0 Hz, 2H), 7.38 (d, J=9.0 Hz, 2H), 5.45 (s, 1H), 5.00 (d, J=12.6 Hz, 1H), 4.92 (d, J=3.6 Hz, 1H), 4.57 (d, J=12.6 Hz, 1H), 3.91 (s, 3H), 1.45 (s, 3H), 0.97 (d, J=7.2 Hz, 3H), and 0.95 (d, J=3.6 Hz, 3H). Anal. (C$_{24}$H$_{32}$O$_7$) C, H.

EXAMPLE 6

Potassium 2-(10-Dihydroartemisininoxy)acetate (Compound 7a)

Ester compound 5a (0.24 g, 0.65 mmol) was dissolved in 10 mL of 2.5% KOH/MeOH solution and allowed to stand at room temperature for 2 days. The solvent was reduced to half volume and diluted with equal volume of H$_2$O. The solution was passed through a reverse-phase column [EM Reagents, Lobar pre-packed column size B (310-25), Lichroprep RP-8, 40–63μ] and eluted with MeOH+H$_2$O (1:1 v/v). The fractions were monitored by reverse-phase TLC (MeOH+H$_2$O 1:1 v/v) and those which contain the desired compound were pooled and the MeOH was evaporated under the reduced pressure. The aqueous solution was lyophilized to give 0.15 g (62%) of white crystals of compound 7a, mp 157°-159° C. Anal. (C$_{17}$H$_{25}$O$_7$K.1.5H$_2$O); C, H.

Prepared by the same procedure were:

Potassium 3-(10-Dihydroartemisininoxy)propionate [compound 7b, 78%, mp 153° C. (dec)]. Anal. (C$_{18}$H$_{27}$O$_7$K.H$_2$O) C, H.

Potassium 4-(10-Dihydroartemisininoxy)butyrate [compound 7c, 40%, mp 142° C. (dec)]. Anal. (C$_{19}$H$_{29}$O$_7$K.H$_2$O) C, H.

Potassium p-(10-Dihydroartemisininoxy)methylbenzoate [compound 7d, 60%, mp 158° C. [dec)]. Anal. (C$_{34}$H$_{29}$O$_7$K.H$_2$) C, H.

3-(10-Dihydroartemisininoxy)propionic Acid (Compound 8b)

Ester compound 5b (0.4 g, 1 mmole) in 10 mL of 2.5% KOH/MeOH solution was allowed to stand at room temperature for 2 days. The solvent was then evaporated to dryness under the reduced pressure. The residue was dissolved in 10 mL of H$_2$O and the solution was washed 2 times with an equal volume of Et$_2$O. The aqueous layer was acidified with AcOH and the mixture was extracted 2 times with Et$_2$O. The Et$_2$O extracts were combined, dried over Na$_2$SO$_4$, and evaporated to dryness. The oily product crystallized from hexane-Et$_2$O to give white crystals (0.25 g, 70%), mp 160°-162° C. IR (KBr) 1740 cm$^{-1}$ (—COOH); $^1$H NMR (CDCl$_3$) δ0.88 (d, J=7.2 Hz, 3H), 0.94 (d, J=3.6 Hz, 3H), 1.44 (s, 3H), 2.62 (t, J=6.3 Hz, 2H), 3.63 (m, 1H), 4.14 (m, 1H), 4.82 (d, J=3.6 Hz, 1H), 5.45 (s, 1H), and 7.92 (br s, 1H). Anal. (C$_{18}$H$_{28}$O$_7$) C, H.

EXAMPLE 7

4-(10-Dihydroartemisininoxy)butyric Acid (Compound 8c)

The same procedure for the preparation of compound 8b was used to prepared compound 8c from compound 5c in 60% yield. The product is an oil; $^1$H NMR (CDCl$_3$) δ0.90 (d, J=7.2 Hz, 3H), 0.96 (d, J=3.6 Hz, 3H), 1.43 (s, 3H), 3.39 (m, 1H), 3.90 (m, 1H), 4.79 (d, J=3.6 Hz, 1H), and 5.39 (s, 1H). Anal. (C$_{19}$H$_{30}$O$_7$.¼H$_2$O) C, H.

EXAMPLE 8

Para-(10-Dihydroartemisininoxy)methylbenzoic Acid (Compound 8d, Artelinic acid)

The same procedure for the preparation of compound 8b was adapted to the preparation of compound 8d from compound 5d in 55% yield. Purification was achieved by recrystallization from MeOH-H$_2$O, mp 142°-145° C.; IR (KBr) 1700 cm$^{-1}$ (—COOH), $^1$H NMR (DCDl$_3$)δ0.96 (d, J=2.7 Hz, 3H), 0.98 (d, J=7.2 Hz, 3H), 1.46 (s, 3H0, 2.71 (m, 1H), 4.60 (d, J=13.5 Hz, 1H), 4.94 (d, J=2.7 Hz, 1H), 5.00 (d, J=13.5 Hz, 1H), 5.46 (s, 1H), 7.42 (d, J=8.1 Hz, 2H), and 8.10 (d, J=8.1 Hz, 2H). Anal. (C$_{23}$H$_{30}$O$_7$.½H$_2$O), C, H.

EXAMPLE 9

Stability Studies of Artelinic (Compound 8d) and Artesunic Acids (Compound 1)

To a 5 mm NMR tube containing 10 mg of sample was added 0.5 mL of 2.5% K$_2$CO$_3$/D$_2$O solution. The initial spectrum of the solution was taken within 5 minutes, and again at intervals thereafter. The extent of hydrolysis was estimated by the following equation:

% Decomposition = $(B/2A+B) \times 100$ where A = integration of H-10 (5.80 ppm, d, J = 10.8 Hz, 1H) and H-12 (5.71 ppm, s, 1H) of artesunate; B = integration of the singlet at 2.42 ppm for the potassium succinate formed. With time, the intensity of potassium succinate (2.42 ppm) signal increases, while that of H-10 and H-12 of artesunate decreases. The stability study of compound 1 in 5% $NaHCO_3/D_2O$ was also carried out by the same procedure.

Materials Test Methods and Results

The new water-soluble dihydroartemisinin derivatives were tested in vitro against 2 clones of human malaria, Plasmodium falciparum D-6 (Sierra Leone clone) and W-2 (Indochina clone). The former clone is a strain that is resistant to mefloquine and the latter, to chloroquine, pyrimethamine, sulfadoxine, and quinine. The results (Table 1) indicate that the new derivatives, like the parent agents compounds 2 and 3, are not cross-resistant to any of the antimalarial agents mentioned above. The derivatives are, in general, more effective against the W-2 than the D-6 strain. Esters (compounds 5a-d) possess activity comparable to that of the parent compounds, compounds 2 and 3, although activity decreases as the aliphatic chain is elongated from 1 (compound 5a) to 3 carbons (compound 5c). Conversion of the esters (compounds 5a-d) to their corresponding carboxylates (compounds 7a-d) or acids (compounds 8b-d), with the exception of compound 7d and compound 8d (artelinic acid, drastically decrease the antimalarial activities in both cell lines.

Overall, the free acids exhibit better in vitro antimalarial activities than their salts, however, compound 7d, the salt form of compound 8d, is not only water soluble and stable in solution, but also possess comparable in vitro activity to artemisinin (compound 3).

The stability studies performed in 2.5% $K_2CO_3/D_2O$ revealed that no detectable change in artelinic acid (compound 8d) occurred after 35 days and less than 3% hydrolyzed after 67 days at room temperature; however, substantial hydrolysis (20%) of artesunic acid (compound 1) occurred within 1.5 hours under identical conditions (Table 3). The rate of hydrolysis of compound 1 in 5% $NaHCO_3/D_2O$ solution was found to be slower than in 2.5% $K_2CO_3/D_2O$. The half-life was estimated to be about 4.5 days in 5% $NaHCO_3$ compared to <1 day in 2.5% $K_2CO_3$ solution.

Laboratory Studies

In vitro assays were conducted using a modification of the semiautomated microdilution technique of Desjardins et al., Antimicrob. Agents Chemoether., 1979, Volume 16, page 710 and Milhous et al., Antimicrob. Agents Chemother., 1985, Volume 27, page 525. Two P. falciparum malaria parasite clones, designated as Indochina (W-2) and Sierra Leone (D-6), were utilized in susceptibility testing. They were derived by direct visualization and micromanipulation from patient isolates obtained by the Centers for Disease Control, Atlanta, GA in 1980 and 1982, respectively. The patients had acquired infections either in Vietnam or Sierra Leone. The Indochina clone is resistant to the antimalarials chloroquine, sulfadoxine, pyrimethamine, and quinine, whereas the Sierra Leone, is resistant to mefloquine but susceptible to chloroquine, quinine, sulfadoxine, and pyrimethamine. Test compounds were initially dissolved in DMSO and 70% ethanol and diluted in RPMI 1640 culture medium with 10% human plasma to 400 fold. Drugs were subsequently further diluted using the Cetus Pro/Pette (Perkin-Elmer Corp., Norwalk, CT) over a range of $1.56-100 \times 10^{-9}$ molar. Parasite inocula (at 0.5% parasitemia and a 1% hematocrit) were incubated for 24 hours and added to equimolar concentrations of each test compound prior to the addition of $^3$H-hypoxanthine. After a further incubation of 18 hours, particulate matter was harvested from each microtiter well using an automated cell harvester (Skatron, Inc., Sterling, VA). Uptake of $^3$H-hypoxanthine was measured using a scintillation spectrophotometer (Model LS3801, Beckman Instruments, Irvine, CA). Concentration-response data were analyzed by nonlinear regression and the $IC_{50}$'s (50% inhibitory concentrations) for each compound were calculated.

In Vivo Antimalarial Studies

The suppressive blood schizonticidal and curative activities of artemisinin, artelinic acid and artesunic acid, were measured in a test where mice were infected with $5.98 \times 10^5$ Plasmodium berghei parasitized cells intraperitoneally on day zero. Test compounds were either dissolved in peanut oil or 5% $NaHCO_3$ and administered subcutaneously once a day for 3 consecutive days commencing on day 3. The dose levels of compounds given were 640, 160, and 40 mg/kg/day. Blood films were taken on days 6, 13, and 20. Blood schizonticidal activity was determined by monitoring blood films for the appearance of parasites and for extended survival times compared to infected untreated controls. Mice surviving 60 days were considered cured. The infected untreated control mice (negative controls) died on either day 6 or 7. Compounds were considered active when the survival time of the treated mice was greater than twice the control mice, i.e., 12 to 14 days. The results of these tests are shown in Table 2.

TABLE 1

In Vitro Antimalarial Activites Against P. falciparum

| Compounds | $IC_{50}$'s (ng/mL) | |
|---|---|---|
| | Sierra Leone (D-6) | Indochina Clone (W-2) |
| 2 | 0.41 | 0.69 |
| 3 | 2.93 | 0.66 |
| 5a | 0.60 | 0.26 |
| 5b | 1.84 | 0.64 |
| 5c | 3.06 | 0.95 |
| 5d | 0.77 | 0.37 |
| 7a | 53.79 | 26.23 |
| 7b | 85.02 | 23.28 |
| 7c | 75.52 | 10.52 |
| 7d | 1.74 | 0.92 |
| 8b | 51.74 | 35.64 |
| 8c | 17.90 | 8.04 |
| 8d | 4.07 | 1.38 |

TABLE 2

60 Days Survival Data

| Compound | Dosage Mg/Kg | Vehicle | Route of Administration | **Number of Cures |
|---|---|---|---|---|
| Artemisinin | *640 | peanut oil | SC | 5/5 |
| | 160 | peanut oil | SC | 5/5 |
| | 40 | peanut oil | SC | 3/5(A)***, 2/5 |
| Artelinic Acid | 640 | 5% $NaHCO_3$ | SC | 5/5 |
| | 160 | 5% $NaHCO_3$ | SC | 5/5 |
| | 40 | 5% $NaHCO_3$ | SC | 5/5 |
| Artesunic Acid | 640 | 5% $NaHCO_3$ | SC | 5/5 |
| | 160 | 5% $NaHCO_3$ | SC | 3/5(A), |

TABLE 2-continued

60 Days Survival Data

| Compound | Dosage Mg/Kg) | Vehicle | Route of Administration | **Number of Cures |
|---|---|---|---|---|
| | 40 | 5% NaHCO$_3$ | SC | 0/5 2/5(A), 0/5 |

*Blood films negative for 640 and 160 mg/kg, positive for 3 of 5 in 40 mg/kg dosage.
**Mean survival of control mice - 6 days.
***A = active. The terms "cure" and "active" are defined in the Experimental Section entitled "In Vivo Antimalarial Studies".

TABLE 3

Stability of Artesunic (Compound 1) and Artelinic (Compound 8d) Acids in 2.5% K$_2$CO$_3$/D$_2$O Solution

| | % Hydrolysis Compounds | |
|---|---|---|
| Time (hours) | 1 | 8d |
| 1.5 | 20 | 0 |
| 24 | 60 | 0 |
| 48 | 75 | 0 |
| 72 | 91 | 0 |
| 96 | 98 | 0 |

TABLE 4

Stability of Artesunic Acid (1) in 5% NaHCO$_3$/D$_2$O at Room Temperature

| Time | % Hydrolysis |
|---|---|
| 4 hours | <5 |
| 2 days | 22 |
| 3 days | 33 |
| 4 days | 45 |
| 8 days | 75 |
| 9 days | 82 |

TABLE 5

| | | Elemental Analyses | | | |
|---|---|---|---|---|---|
| | | Calculated | | Found | |
| Compound | Formula | C | H | C | H |
| 5a | C$_{19}$H$_{30}$O$_7$ | 61.62 | 8.11 | 62.09 | 8.09 |
| 5b | C$_{19}$H$_{30}$O$_7$ | 61.62 | 8.11 | 62.03 | 8.07 |
| 5c | C$_{20}$H$_{32}$O$_7$ | 62.50 | 8.33 | 63.13 | 87.64 |
| 5d | C$_{24}$H$_{32}$O$_7$ | 66.67 | 7.41 | 66.85 | 7.60 |
| 7a | C$_{17}$H$_{25}$O$_7$K 1.5H$_2$O | 50.12 | 6.88 | 50.14 | 6.80 |
| 7b | C$_{18}$H$_{27}$O$_7$K H$_2$O | 52.43 | 7.04 | 52.09 | 6.96 |
| 7c | C$_{19}$H$_{29}$O$_7$K ⅜H$_2$O | 54.28 | 7.14 | 54.07 | 7.24 |
| 7d | C$_{23}$H$_{29}$O$_7$K H$_2$O | 58.23 | 6.54 | 58.13 | 6.47 |
| 8b | C$_{18}$H$_{28}$O$_7$ | 60.67 | 7.87 | 60.81 | 8.08 |
| 8c | C$_{19}$H$_{30}$O$_7$ ¼H$_2$O | 60.88 | 8.15 | 60.82 | 8.59 |
| 8d | C$_{23}$H$_{30}$O$_7$ ½H$_2$O | 64.64 | 7.26 | 64.87 | 7.31 |

We claim:
1. A compound represented by the formula

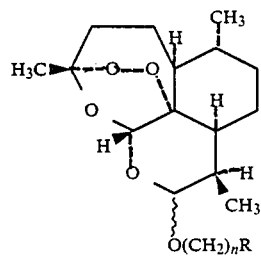

or a pharmaceutically-acceptable salt thereof wherein R is

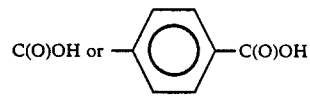

and n represents the positive integers 1 to 7.

2. The compound of claim 1 wherein n represents the positive integers 1,2 or 3.
3. The compound of claim 2 wherein R is C(O)OH and n is 1.
4. The compound of claim 2 wherein R is C(O)OH and n is 2.
5. The compound of claim 2 wherein R is C(O)OH and n is 3.
6. The compound of claim 2 wherein R is

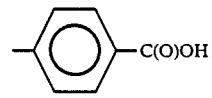

and n is 1.

7. A method for pretreating animals prior to malarial infection with a therapeutically-effective amount of a composition of claim 1.
8. A method for post-treating animals which are infected with malaria with a therapeutically-effective amount of a composition of claim 1.

* * * * *